(12) United States Patent
Zhang

(10) Patent No.: US 11,376,372 B2
(45) Date of Patent: Jul. 5, 2022

(54) DISPOSABLE INJECTION NEEDLE

(71) Applicant: Tianjin Huahong Technology Co., Ltd., Tianjin (CN)

(72) Inventor: Libo Zhang, Tianjin (CN)

(73) Assignee: Tianjin Huahong Technology Co., Ltd., Tianjin (CN)

(*) Notice: Subject to any disclaimer, the term of this patent is extended or adjusted under 35 U.S.C. 154(b) by 114 days.

(21) Appl. No.: 16/427,822

(22) Filed: May 31, 2019

(65) Prior Publication Data

US 2019/0381254 A1    Dec. 19, 2019

(30) Foreign Application Priority Data

Jun. 1, 2018  (CN) .......................... 201810559378.3

(51) Int. Cl.
*A61M 5/32* (2006.01)
*A61M 5/34* (2006.01)

(52) U.S. Cl.
CPC .......... *A61M 5/326* (2013.01); *A61M 5/3202* (2013.01); *A61M 5/3271* (2013.01); *A61M 5/34* (2013.01); *A61M 2005/3247* (2013.01)

(58) Field of Classification Search
CPC .... A61M 5/321; A61M 5/326; A61M 5/3243; A61M 5/3271; A61M 2005/3247; A61M 2005/3267

See application file for complete search history.

(56) References Cited

U.S. PATENT DOCUMENTS 6,884,237 B2 *  4/2005  Asbaghi ............... A61M 5/3272
                                                  604/192
8,961,470 B2 *  2/2015  Schraga ................ A61M 5/347
                                                  604/198

(Continued)

FOREIGN PATENT DOCUMENTS

WO      2014010503 A1    1/2014

OTHER PUBLICATIONS

Extended European Search Report in Corresponding EP Application No. 19177710.1 dated Nov. 4, 2019. 8 pages.

(Continued)

*Primary Examiner* — Laura A Bouchelle
(74) *Attorney, Agent, or Firm* — Leason Ellis LLP

(57) ABSTRACT

The present disclosure relates to a disposable injection needle, including: a needle mount, having a tube needle; a first sleeve, one end of which is suitable for connecting to the needle mount to form receiving space, and the other end of which is provided with a first opening; a second sleeve, one end of which is located inside the receiving space, and the other end of which having a second opening extends out from the first opening, wherein the second sleeve is axially slideable; an elastic element adapted to allow the second sleeve to move axially toward outside the receiving space, wherein: the second sleeve is provided with a sleeve guiding portion, and the needle mount is provided with a guiding engagement portion, the sleeve guiding portion engages with the guiding engagement portion to guide the circumferential rotation of the second sleeve based on axial movement of the second sleeve toward inside of the receiving space; the first sleeve is provided with a blocking member and the second sleeve is provided with a fastener, wherein the blocking member and the fastener are arranged to allow the fastener to pass through the blocking member in the axial direction toward the second opening, and to prevent the (Continued)

G-G fastener from passing through the blocking member in the axial direction away from the second opening to prevent the tube needle from being exposed via the second opening.

17 Claims, 12 Drawing Sheets

(56) References Cited

U.S. PATENT DOCUMENTS

| | | | |
|---|---|---|---|
| 9,138,546 B2* | 9/2015 | Schubert | A61M 5/326 |
| 2005/0113750 A1* | 5/2005 | Targell | A61M 5/3272 |
| | | | 604/110 |
| 2009/0259178 A1 | 10/2009 | Brechbuehler et al. | |
| 2014/0243755 A1 | 8/2014 | Slemmen et al. | |
| 2017/0182260 A1 | 6/2017 | Schraga | |

OTHER PUBLICATIONS

Office Action and English translation for corresponding Chinese Application No. 201810559378.3, dated Jun. 16, 2021. 16 pages.
Office Action and English translation for corresponding Chinese Application No. 201810559378.3, dated Feb. 14, 2022. 16 pages.

* cited by examiner

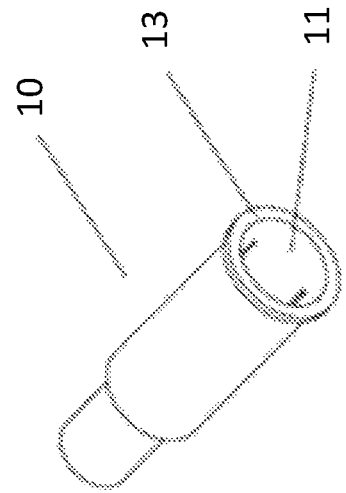
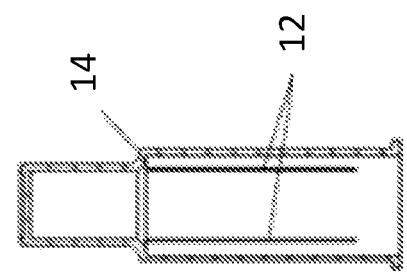
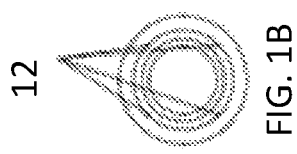
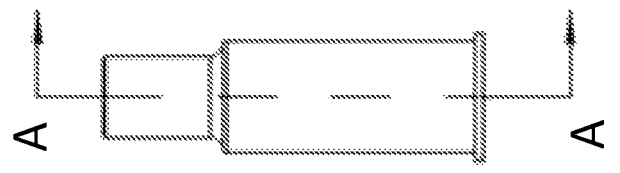

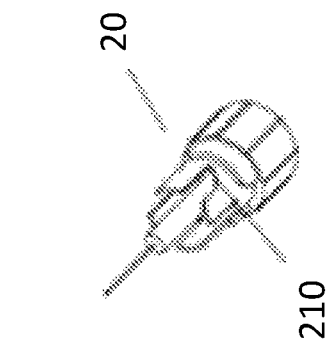
FIG. 2E
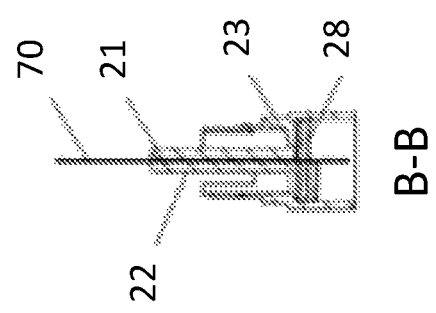
FIG. 2D
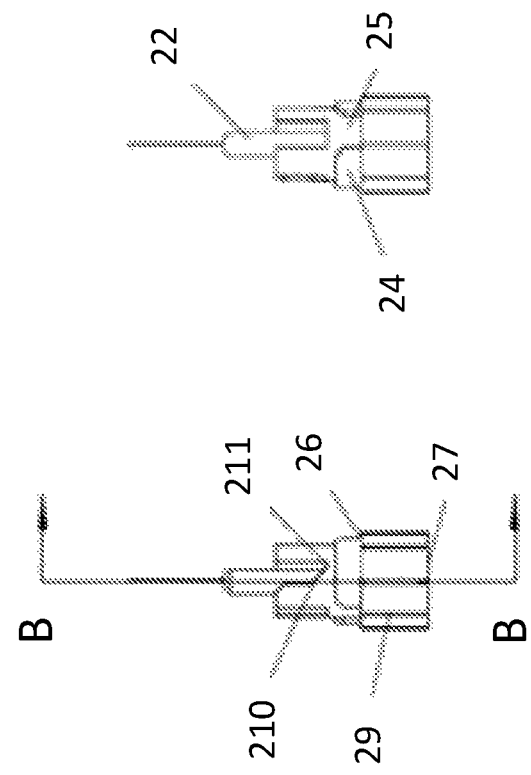
FIG. 2C
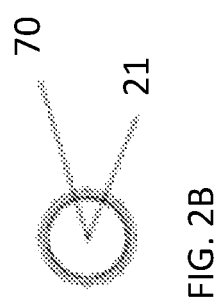
FIG. 2B
FIG. 2A

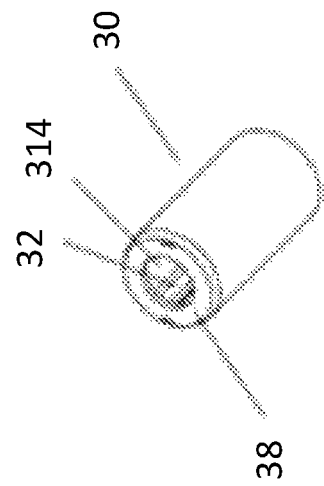
FIG. 3E
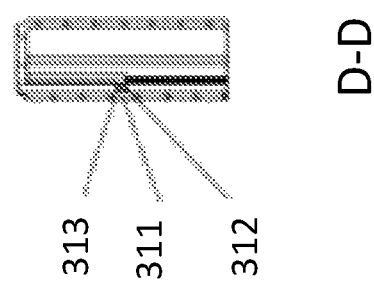
FIG. 3D
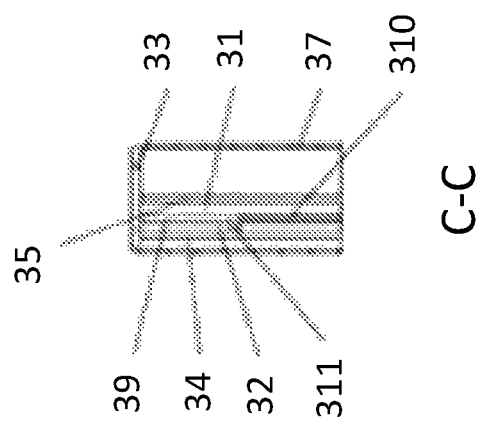
FIG. 3C
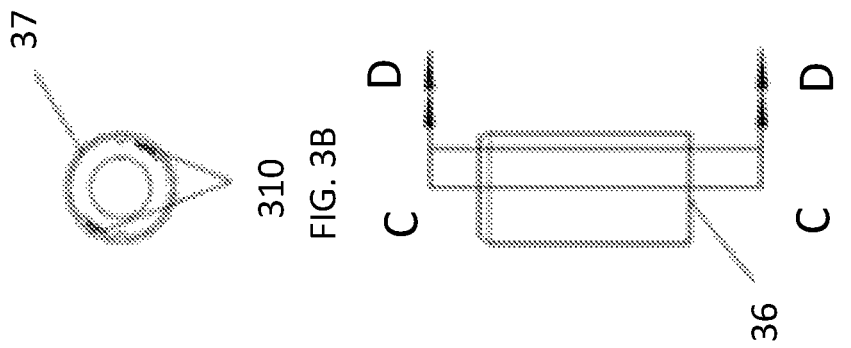
FIG. 3B
FIG. 3A

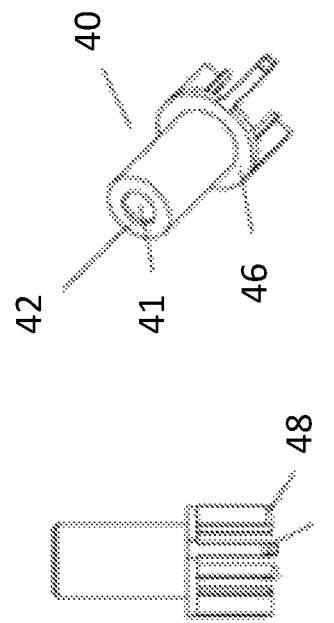
FIG. 4E
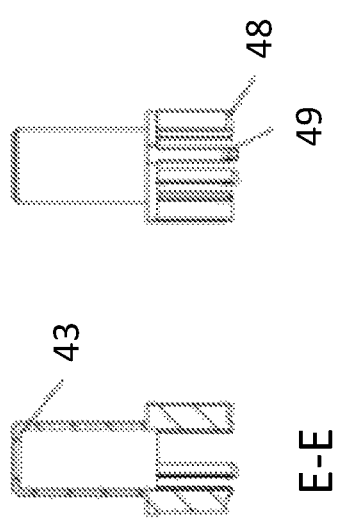
FIG. 4D
FIG. 4C
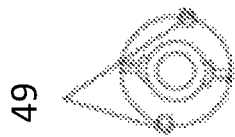
FIG. 4B
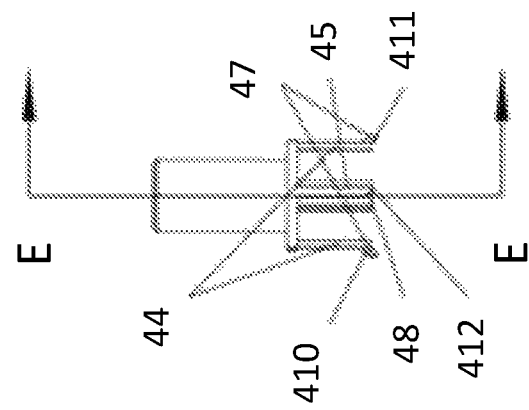
FIG. 4A

G-G

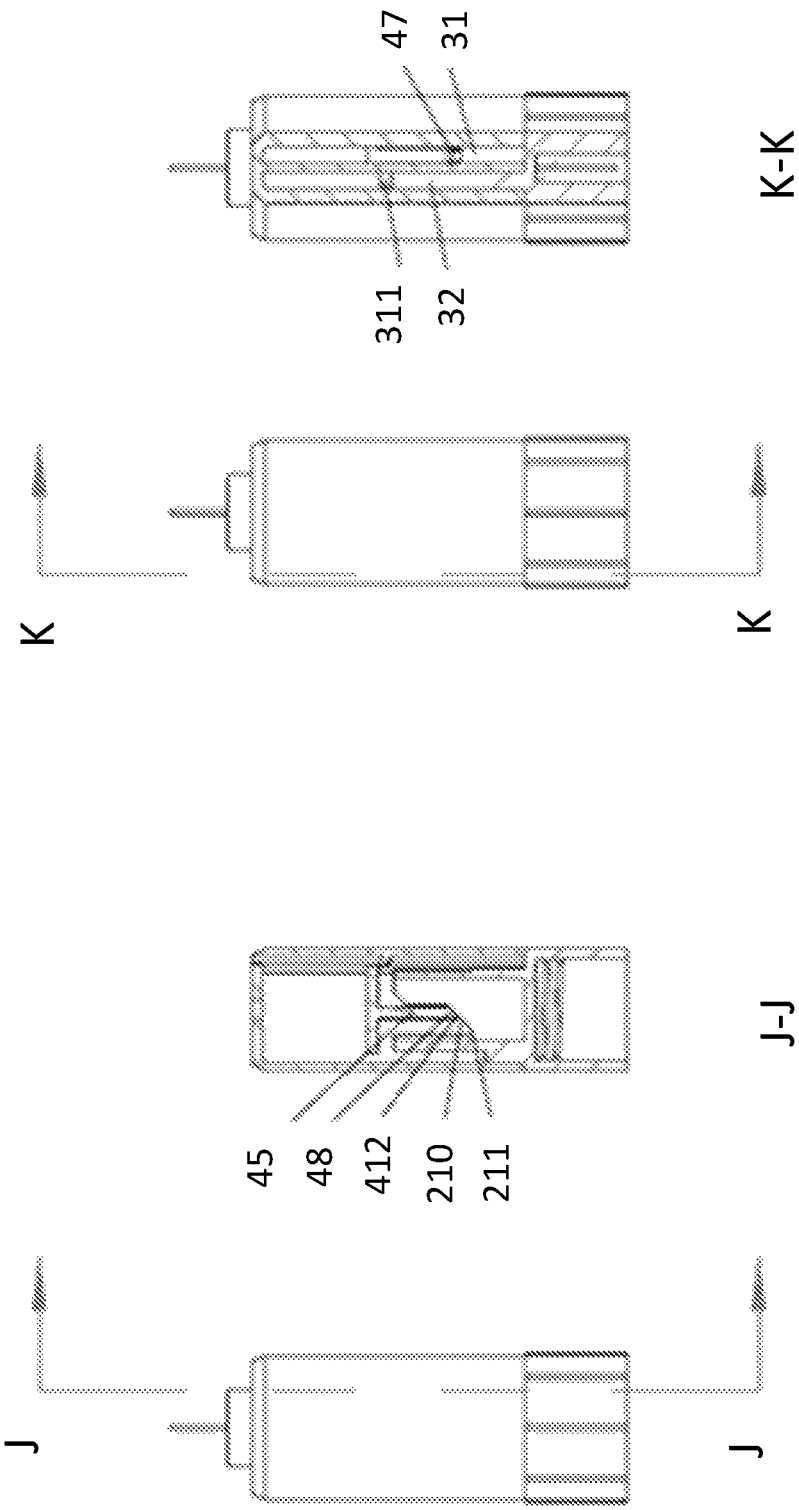

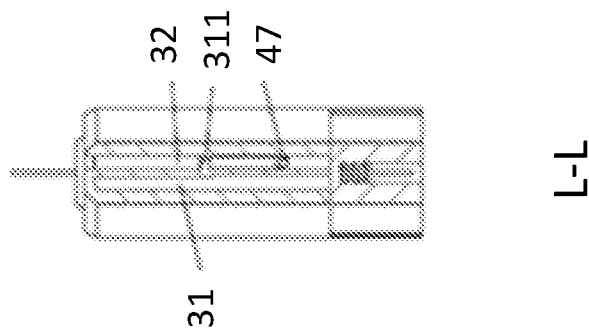
FIG. 10D L-L
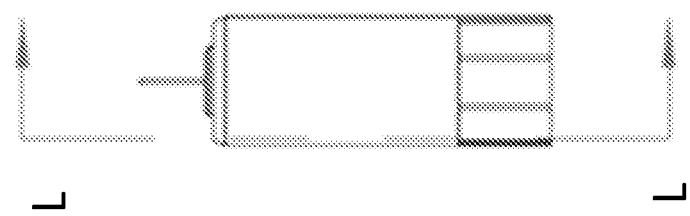
FIG. 10C
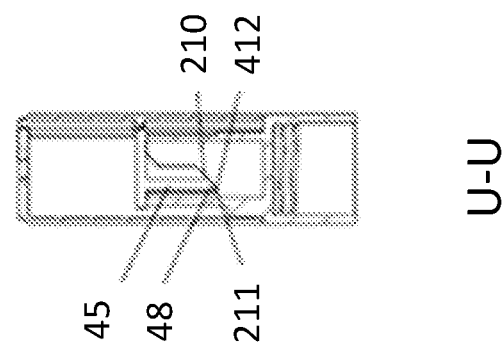
FIG. 10B U-U
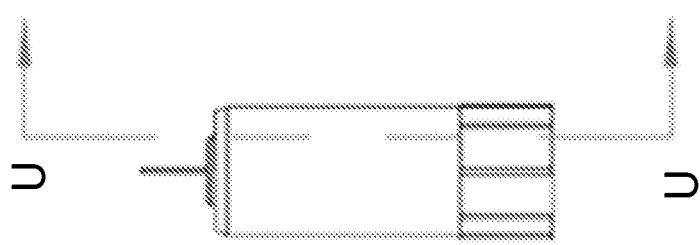
FIG. 10A

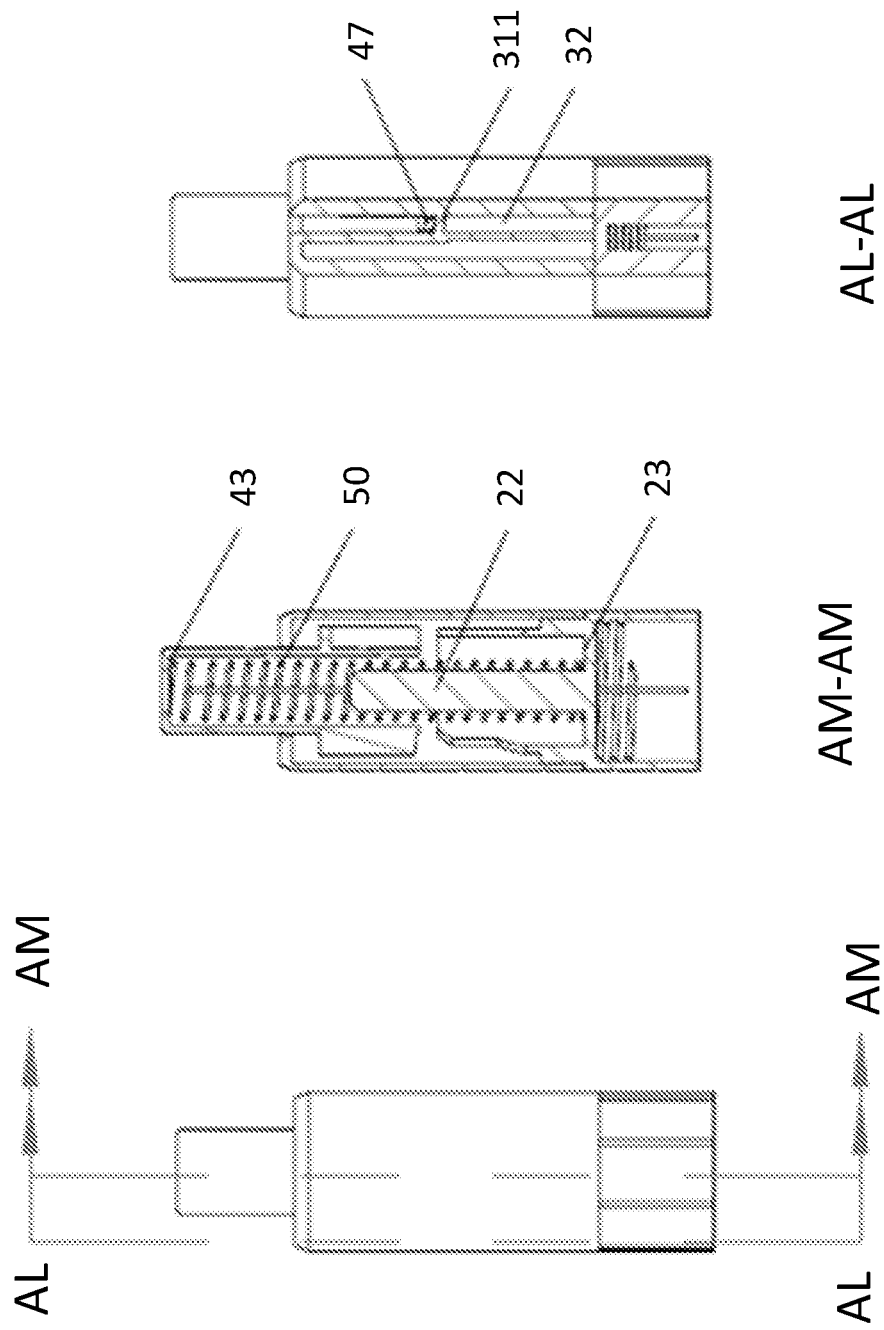

DISPOSABLE INJECTION NEEDLE

CROSS-REFERENCE TO RELATED PATENT APPLICATIONS

This application is claims the benefit of priority of Chinese Patent Application number 201810559378.3 filed Jun. 1, 2018, which is incorporated by reference in its entirety.

TECHNICAL FIELD

The embodiment of the present disclosure relates to the field of medical instruments, more particularly, to a disposable injection needle.

BACKGROUND

Conventional injection needle which is common in the market and cooperates with an insulin injection pen, comprises a big sleeve, a small sleeve, a needle mount, a tube needle and dialyzing paper. The needle tip of the tube needle will be exposed all the time once the big sleeve and the small sleeve are removed, which increases the infection probability for the patients because of secondary use, and the used needle is apt to accidentally injure other people and thus causes cross-infection.

In addition, the big sleeve tends to slide outside the needle mount when the injection needle is being engaged with the injection pen, leading to poor working conditions, for instance unstable assembling.

SUMMARY

The present disclosure is proposed to alleviate or solve at least one aspect of the above problems.

According to one aspect of the embodiments in the present disclosure, the present disclosure provides a disposable injection needle, which comprises:

a needle mount provided with a tube needle that extends axially therethrough;

a first sleeve, one end of which is suitable for connecting to one end of the needle mount to form receiving space between the first sleeve and the needle mount, and the other end of the first sleeve is provided with a first opening;

a second sleeve, one end of which is located inside the receiving space, and the other end of which having a second opening, extends out from the first opening, wherein part of the second sleeve is provided, in an axially slideable manner, inside the receiving space, and the tube needle is adapted to protrude through the second opening;

an elastic element adapted to provide elastic force for the second sleeve to move axially toward outside the receiving space, and the second sleeve is adapted to retract inward the receiving space based on an external force overcoming the elastic force, thus to expose the tube needle, wherein:

the second sleeve is provided with a sleeve guiding portion, and the needle mount or first sleeve is provided with a guiding engagement portion, the sleeve guiding portion engages with the guiding engagement portion to guide circumferential rotation of the second sleeve based on axial movement of the second sleeve toward inside the second sleeve;

the first sleeve is provided with a blocking member and the second sleeve is provided with a fastener, wherein the blocking member and the fastener are arranged to allow the fastener to pass through the blocking member in the axial direction toward the second opening, and to prevent the fastener from passing through the blocking member in the axial direction away from the second opening to prevent the tube needle from being exposed via the second opening.

Alternatively, the inner wall of the first sleeve is provided with a limit guiding slot in which the blocking member is provided; and the fastener is adapted to enter the limit guiding slot due to the rotation of the second sleeve in circumferential direction. Further, the inner wall of the first sleeve is provided with a first guiding rib, a second guiding rib and a third guiding rib which extend in the axial direction and are spaced apart from one another and parallel to one another, wherein a first guiding groove is formed between the first guiding rib and the second one, and a second guiding groove, constituting the limiting guiding slot, is formed between the second guiding rib and the third one; due to the circumferential rotation, the fastener is adapted to move circumferentially from the first guiding groove to the second guiding groove. Furthermore, corresponding to the circumferential movement, one side of the second guiding rib facing the first guiding groove is provided with a face that facilitates moving of the fastener across the second guiding rib; and/or one side of the fastener facing the second guiding rib is provided with a face that facilitates moving of the fastener across the second guiding rib. Further, the cross section of the portion of the second guiding rib, from the blocking member to the first opening is a rectangle, and the cross section of the portion of the second guiding rib, from the blocking member to the end of the first sleeve, is a right trapezoid, with the hypotenuse of the right trapezoid facing the first guiding groove.

Alternatively, the needle mount is provided with a guiding engagement portion; the needle mount is provided with a needle mount guiding portion, the end of which is provided with a needle mount guiding slope which constitutes the guiding engagement portion; the second sleeve includes a sleeve guiding arm which is adapted to move axially and circumferentially inside the needle mount guiding portion, and the end of the sleeve guiding arm is provided with an engaging slope which engages with the needle mount guiding slope and which constitutes the sleeve guiding portion; and the distance or the width of the needle mount guiding portion is greater than that of the sleeve guiding arm in the circumferential direction, so as to allow the second sleeve to complete the circumferential rotation. further, the end of the needle mount guiding portion is additionally provided with a pressing blocking face connected to the needle mount guiding slope; the end of the sleeve guiding arm is provided with an engagement blocking face which is connected to the engaging slope, and which abuts against the pressing blocking face to prevent the second sleeve from moving axially further after the second sleeve completes its circumferential rotation.

Alternatively, the second sleeve is provided with a sleeve limit arm, whose end is provided with the fastener. Further, the side of the fastener facing the second opening is set as a compliant face, and the other side of the fastener facing the compliant face in the axial direction is set as a blocking face; besides, the side of blocking member facing the first opening is set as a blocking face engaging with the blocking face of the fastener; or, the side of the blocking member facing the first opening is set as a blocking face engaging with the blocking face of the fastener, and the other side of the blocking member opposite to the its blocking face in the axial direction is provided with a compliant face cooperating with the compliant face of the fastener.

Alternatively, the first sleeve is provided with a guiding groove and limit guiding slot; the first sleeve is provided with the guiding engagement portion, which is an inclined guiding slot or a cambered guiding slot connecting the end of guiding groove and that of the limit guiding slot; the second sleeve includes a sleeve guiding arm, wherein the fastener is provided at the end of the sleeve guiding arm, and the blocking member is provided inside the limit guiding slot; and the fastener is adapted to enter the limit guiding slot via the inclined guiding slot or the cambered guiding slot due to the circumferential rotation.

Alternatively, the first end of the needle mount is provided with an elastic element limiting column, which extends axially from the first end of the needle mount, and through which the tube needle extends axially; the other end of the second sleeve has a second blocking face, which is perpendicular to the axis and defines the second opening; the elastic element includes a spring, one end of which is provided to the elastic element limiting column and the other end of which presses against the second blocking face.

Alternatively, one end of the elastic element is fixed to the first sleeve and the other end of the elastic element is fixed to the needle mount, and the elastic element provides the elastic pulling force causing the needle mount to move axially toward outside the receiving space.

Alternatively, one end of second sleeve is located inside the receiving space and the other end of the second sleeve is provided with the second opening and extends out from the first opening, and one part of the second sleeve is provided in an axially slideable manner inside the receiving space. Further, the second sleeve has a small-diameter section and a large-diameter section connected to each other axially, a step surface is formed at the junction there between, wherein, the small-diameter section is suitable for axially extending out of the first sleeve from the first opening, and the distal end of the small-diameter section has the second opening and the second blocking face which is perpendicular to the axis and defines the second opening, the step surface is adapted to abut against the first blocking face, while the large-diameter section is provided in an axially slideable manner inside the receiving space.

Alternatively, the first end of the needle mount is additionally provided with an engaging circumferential surface; and one end of the first sleeve is suitable for being sleeve-jointed to the engaging circumferential surface.

Alternatively, the disposable injection needle further includes a third sleeve, which sleeve-joints the needle mount, the first sleeve and the second sleeve from outside. Further, a first anti-rotational mechanism is provided at the junction between the first sleeve and the needle mount, and a second anti-rotational mechanism is provided at the junction between the third sleeve and the needle mount. Further, the disposable injection needle also includes dialyzing paper, which is provided to cover the opening of the third sleeve.

Alternatively, the other end of the needle mount is provided with a connecting device suitable to connect with the injection pen.

Alternatively, the second sleeve is provided with two guiding portions and two limit arms, wherein the two limit arms are arranged to be opposite to each other in the radial direction, and the two guiding portions are arranged to be opposite to each other in the radial direction.

In the embodiments of the present disclosure, with the internal structure design of the injection needle assembly, the needle tip of the tube needle will not be exposed to the outside after being used.

BRIEF DESCRIPTION OF DRAWINGS

FIGS. 1a, 1b, 1c, 1d are respectively a front view, an upward view, a sectional view and a stereoscopic view of the big sleeve (the third sleeve) according to one exemplary embodiment of the present disclosure.

FIGS. 2a, 2b, 2c, 2d, 2e are respectively a front view, an upward view, a left view, a sectional view and a stereoscopic view of the needle mount according to one exemplary embodiment of the present disclosure.

FIGS. 3a, 3b, 3c, 3d, 3e are respectively a front view, an upward view, a C-C sectional view, a D-D sectional view and a stereoscopic view of the auxiliary sleeve (the first sleeve) according to one exemplary embodiment of the present disclosure.

FIGS. 4a, 4b, 4c, 4d, 4e are respectively a front view, an upward view, a sectional view, a left view and a stereoscopic view of the small sleeve (the second sleeve) according to one exemplary embodiment of the present disclosure.

FIGS. 9a, 9b, 9c, 9d are respectively a front view, a J-J sectional view, a left view and a K-K sectional view of the injection needle with the big sleeve being removed which just contacts user's skin, according to one exemplary embodiment of the present disclosure.

FIGS. 10a, 10b, 10c, 10d are respectively a front view, a U-U sectional view, a left view and a L-L sectional view of the injection needle with the big sleeve being removed, wherein the needle tip pierces into user's skin, according to one exemplary embodiment of the present disclosure.

FIGS. 12a, 12b, 12c are respectively a front view, an AM-AM view showing the spring state and an AL-AL sectional view of the injection needle after the injection, according to one exemplary embodiment of the present disclosure.

DETAILED DESCRIPTION OF EXEMPLARY EMBODIMENTS

Figure 6:
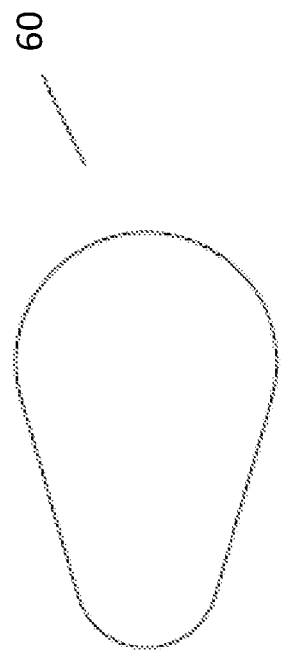
FIG. 6 is the front view of the dialyzing paper according to one exemplary embodiment of the present disclosure.

The technical solutions of the present disclosure will be further described below, with reference to the embodiments and the accompanying drawings. In the specification, the same or analogous drawings reference numerals indicate the same or analogous components. The following explanation of the present disclosure embodiment, with reference to attached drawings, is intended to explain the inventive concept of the present disclosure and should not be understood as a limitation to the present disclosure.

Figure 5:
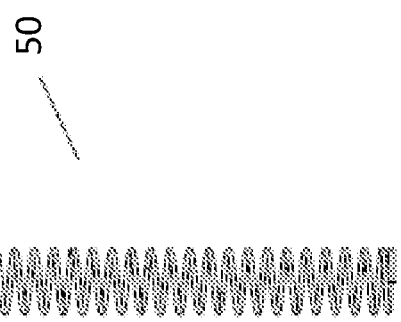
FIG. 5 is the view of the elastic element according to one exemplary embodiment of the present disclosure.

Firstly, with reference to the drawings, the injection needle according to one exemplary embodiment of the present disclosure, is described in detail, and it is noted that that, for the sake of clarity, some features or elements in the figures are not specifically illustrated. As shown in the figures, the injection needle, according to one exemplary embodiment of the present disclosure, comprises:

a needle mount 20, as shown in FIGS. 2a-2d, which is provided with a tube needle 70 extending axially therethrough;

a first sleeve 30, as shown in FIGS. 3a-3e and FIGS. 7a-7c, one end of which is suitable for connecting to one end of the needle mount 20 to form a receiving space R between the first sleeve 30 and the needle mount 20, and the other end of which is provided with a first opening 314;

a second sleeve 40, as shown in FIGS. 4a-4e and 7a-7c, one end of which is located inside the receiving space R, and the other end of which having a second opening 41 extends out from the first opening 314, and part of the second sleeve 40 is provided in an axially slideable manner inside the receiving space R, and the tube needle 70 is adapted to protrude through the second opening 41;

a spring 50 (referring to FIG. 5) which is adapted to provide elastic force to allow the second sleeve 40 to move axially toward outside the receiving space, wherein the second sleeve 40 is adapted to retract inward the receiving space based on an external force overcoming the elastic force, so as to expose the tube needle 70, wherein:

referring to FIGS. 2a-2d, FIGS. 4a-4e, FIGS. 9a-9d and FIGS. 10a-10c, the second sleeve 40 is provided with a sleeve guiding portion 48, the needle mount 20 is provided with a guiding engagement portion 210, and the sleeve guiding portion 48 engages with the guiding engagement portion 210 to guide the circumferential rotation of the second sleeve 40 based on axial movement of the second sleeve 40 toward inside the receiving space R;

as shown in FIGS. 9a-9d, the first sleeve 30 is provided with a blocking member 311, and as shown in FIG. 4a-4e, the second sleeve 40 is provided with a fastener 47, wherein the blocking member 311 and the fastener 47 are arranged to allow the fastener 47 to pass through the blocking member 311 in the axial direction toward the second opening 41, and to prevent the fastener 47 from passing through the blocking member 311 in the axial direction away from the second opening 41 to prevent the tube needle 70 from being exposed via the second opening 41.

Figure 11B:
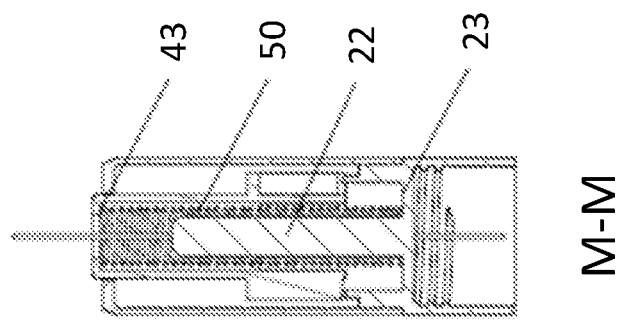
FIGS. 11a, 11b are respectively a front view and a M-M sectional view showing the spring state of the injection needle with the big sleeve being removed, wherein the needle tip pierces into user's skin, according to one exemplary embodiment of the present disclosure.
Figure 11A:
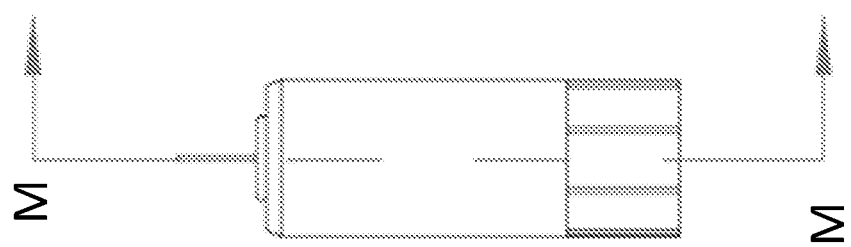

In the embodiments described above, the second sleeve 40 moves axially toward inside the receiving space R and rotates circumferentially at the same time, where it can be considered that the tube needle has being exposed and an injection can be carried out or to be fulfilled, as shown in FIGS. 9-11; later, the second sleeve 40 is pushed toward outside due to the spring 50, so that the fastener 47 can move across the blocking member 311, where, as shown in FIG. 12a, the tube needle 70 is located inside the second sleeve 40, in this case, however, even if the second sleeve 40 is pressed toward inside the receiving space R, the tube needle 70 will not be exposed because the fastener 47 is blocked by the blocking member 311, as shown in FIG. 12c. Therefore, the above technical solution can prevent secondary use of the injection needle and can also prevent the tube needle from accidentally piercing or injuring after use.

In an alternative embodiment, as shown in FIGS. 3a-3e, the inner wall of the first sleeve 30 is provided with a limit guiding slot 32 in which the blocking member 311 is provided; and the fastener 47 enters the limit guiding slot 32 due to the circumferential rotation of the second sleeve 40.

However, it is to be noted that, the limit guiding slot herein can be interpreted widely except what is shown in the figures, for example, in the case where the blocking member circumferentially extends a certain distance on the inner wall of the first sleeve 30, the fastener 47 needs to pass through the blocking member 311 or be blocked by the blocking member 311 in the axial direction thus, the axial portion on the inner wall of the first sleeve 30 that the blocking member is positioned, can also be referred to as a limit guiding slot, and is within the scope of the present disclosure.

As shown in FIGS. 3a-3e, the inner wall of the first sleeve 30 is provided with the first guiding rib 35, the second guiding rib 39 and the third guiding rib 34 which extend in the axial direction and are spaced apart from one another and parallel to one another, wherein the first guiding groove 31 is formed between the first guiding rib 35 and the second guiding rib 39, and a second guiding groove, constituting the limit guiding slot 32, is formed between the second guiding rib 39 and the third guiding rib 34. Correspondingly, due to the circumferential rotation, the fastener 47 is adapted to move circumferentially from the first guiding groove 31 to the second guiding groove.

In a further embodiment, the following solution may facilitate moving of the fastener 47 across the second guiding rib 39: corresponding to the circumferential movement, one side of the second guiding rib 39 facing the first guiding groove 31 is provided with a face that facilitates moving of the fastener 47 across the second guiding rib 39; and/or one side of the fastener 47 facing the second guiding rib 39 is provided with a face that facilitates moving of the fastener 47 across the second guiding rib 39. In a further alternative embodiment, the cross section of the portion of the second guiding rib 39, from the blocking member 311 to the first opening (the upper part of the blocking member 311 in FIG. 3c), is a rectangle, and the cross section of the portion of the second guiding rib 39, from the blocking member 311 to the end of the first sleeve 30 (the lower part of the blocking member in FIG. 3c), is a right trapezoid, with the hypotenuse 310 of the right trapezoid facing the first guiding groove 31.

In an alternative embodiment, as shown in FIGS. 2a-2e, the needle mount 20 is provided with a guiding engagement portion 210; the needle mount 20 is provided with a needle mount guiding portion, the end of which is provided with a needle mount guiding slope which constitutes the guiding engagement portion 210; as shown in FIGS. 4a-4e and 9a-9d, the second sleeve 40 includes a sleeve guiding arm 45 which is adapted to move axially and circumferentially inside the needle mount guiding portion, and the end of the sleeve guiding arm 45 is provided with an engaging slope which engages with the needle mount guiding slope 210, which constitutes the sleeve guiding portion 48, in addition, with reference to FIG. 9b, the distance or the width of the needle mount guiding portion is greater than that of the sleeve guiding arm 45 in the circumferential direction, so as to allow the second sleeve 40 to complete the circumferential rotation.

In a further alternative embodiment, as shown in FIG. 9b, the end of the needle mount guiding portion is additionally provided with a pressing blocking face 211 connected with the needle mount guiding slope 210; the end of the sleeve guiding arm 45 is provided with an engagement blocking face 412 which is connected to the engaging slope 48 and which abuts against the pressing blocking face 211 to prevent the second sleeve 40 from moving axially further after the second sleeve 40 completes its circumferential rotation.

It should be pointed out that, the technical solution in which the engagement blocking face 412 or the pressing blocking face 211 is omitted, is also within the scope of the present disclosure.

As shown in FIGS. 4a-4e, the second sleeve 40 is provided with a sleeve limit arm 44 whose end is provided with the fastener 47.

In a further embodiment, the fastener and the blocking member can be provided so that the moving of fastener across the blocking member can be easily blocked by the blocking member after the fastener moves across the blocking member.

Accordingly, as shown in FIGS. 4a-4e, the side of the fastener 47 facing the second opening (the upside in FIG. 4a) is set as a compliant face 410, and the other side of the fastener facing the compliant face in the axial direction is set as a blocking face 411, the compliant face 410 herein refers to the face that can be easily passed through, while the blocking face 411 refers to the face that blocks other parts to pass through. In the embodiment, the compliant face can be an inclined one whose inclined direction is adapted to the moving direction, and the blocking face may be a slope too, however, the inclined direction of the blocking face is against the moving direction.

Accordingly, as shown in FIGS. 3a-3e, the side of the blocking member 311 facing the first opening (the upside of the blocking member in FIG. 3d) is set as a blocking face 313 engaging with the blocking face 411 of the fastener 47; or, the side of the blocking member facing the first opening (the upside of the blocking member in FIG. 3d) is set as a blocking face 313 engaging with the blocking face 411 of the fastener 47, and the other side of the blocking member 311 opposite to its blocking face 313 in the axial direction (the downside of the blocking member in FIG. 3d) is provided with a compliant face 312 cooperating with the compliant face 410 of the fastener 47.

In addition, in an alternative embodiment, to facilitate moving of the fastener 47 across the guiding rib 39, the side of the fastener 47 facing the guiding rib 39 when the fastener is in the first guiding groove 31 is provided with a fastener slope 49.

Though it is not shown, in an alternative embodiment of the present disclosure, a guiding engagement portion can be provided to the first sleeve. Specifically, the first sleeve is provided with a guiding groove and a limit guiding slot; the first sleeve is provided with the guiding engagement portion which is an inclined guiding slot or a cambered guiding slot connecting the end of the guiding groove and that of the of limit guiding slot; the second sleeve includes a sleeve guiding arm, wherein the fastener is provided at the end of the sleeve guiding arm, and the blocking member is provided inside the limit guiding slot; due to the circumferential rotation, the fastener enters the limit guiding slot via the inclined guiding slot or the cambered guiding slot. In the above embodiment, the first sleeve guides the axial movement and circumferential rotation of the second sleeve, and when the second sleeve is pressed inward, the guiding groove guides the second sleeve to move axially, and as the second sleeve moves axially, the sleeve guiding arm enters the inclined guiding slot or the cambered guiding slot, and during the subsequent axial movement the circumferential rotation of the sleeve guiding arm is completed, and then the sleeve guiding arm enters the limit guiding slot.

The following is the illustration of the installation of the elastic element 50. As shown in FIGS. 2a-2e and FIG. 7b, in the embodiment of the present disclosure, the first end of the needle mount 20 is provided with an elastic element limiting column 22, which extends axially from the first end of the needle mount 20, and through which the tube needle 70 extends axially. As shown in FIG. 7b, the other end of the second sleeve 40 has a second blocking face 43, which is perpendicular to the axis and defines the second opening; the elastic element includes a spring, one end of which is provided to the elastic element limiting column 22 and the other end of which presses against the second blocking face 43. It should be pointed out that, the elastic element 50 is not necessarily to abut the end face from which the spring limiting column of the needle mount 20 extends, as long as one end of the elastic element can be fixed to the elastic element limiting column. However, in a further embodiment, as shown in FIG. 7b, the elastic element 50 can be relatively loosely sleeve-jointed to the spring limiting column 22 so as to deform in the entire spring length.

In an alternative embodiment of the present disclosure, the elastic element can also be installed by other means. For example, one end of the elastic element is fixed to the first sleeve and the other end of the elastic element is fixed to the needle mount, the elastic element provides the elastic pulling force causing the needle mount to move axially toward outside the receiving space.

In an alternative embodiment of the present disclosure, one end of the second sleeve 40 is located inside the receiving space R, and the other end of the second sleeve is provided with a second opening and extends out from the first opening, and one part of the second sleeve is provided in an axially slideable manner inside the receiving space. In a further embodiment, as shown in FIGS. 4a-4e and FIG. 7b, the second sleeve has a small-diameter section and a large-diameter section connected to each other axially, a step surface 46 is formed at the junction therebetween, wherein, the small-diameter section is suitable for axially extending out the first sleeve from the first opening, and the distal end of the small-diameter section has the second opening and the second blocking face which is perpendicular to the axis and defines the second opening, the step surface is adapted to abut against the first blocking face, and the large-diameter section is provided in an axially slideable manner inside the receiving space.

In an alternative embodiment of the present disclosure, as shown in FIGS. 2a-2e, the first end of the needle mount is additionally provided with an engaging circumferential surface 24; one end of the first sleeve 30 is suitable for being sleeve-jointed to the engaging circumferential surface 24.

In an alternative embodiment of the disclosure, the injection needle also includes a third sleeve 10, which sleeve-joints the needle mount 20, the first sleeve 30 and the second sleeve 40 from outside.

Alternatively, a first anti-rotational mechanism is provided at the junction between the first sleeve and the needle mount (such as a rib or a protrusion, or interference fitting configuration), and a second anti-rotational mechanism (such as anti-rotating rib 12 or protrusion, or interference fitting configuration) is provided at the junction between the third sleeve and the needle mount.

Alternatively, the injection needle also includes dialyzing paper 60, which covers the opening of the third sleeve.

Alternatively, the other end of the needle mount 20 is provided with a connecting device suitable to connect with the injection pen. The connecting device can be a thread 28, as shown in FIGS. 2a-2e.

It should be pointed out that, in the present disclosure, a bar or a rib only differs from one another slightly in size, otherwise, they should be considered as the same, in other words, it could be considered that a bar and a rib have essentially the same meaning in the present disclosure.

Figure 7C:
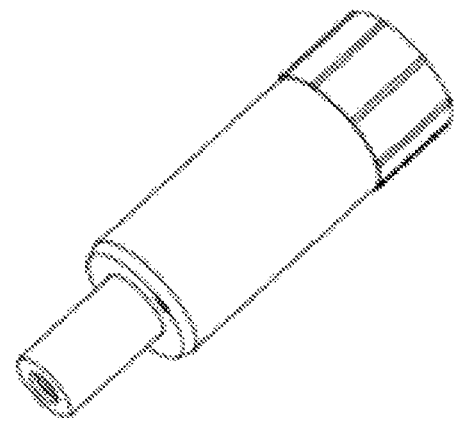
FIGS. 7a, 7b, 7c are respectively a front view, a sectional view and a stereoscopic view of the injection needle without the big sleeve according to one exemplary embodiment of the present disclosure.
Figure 7B:
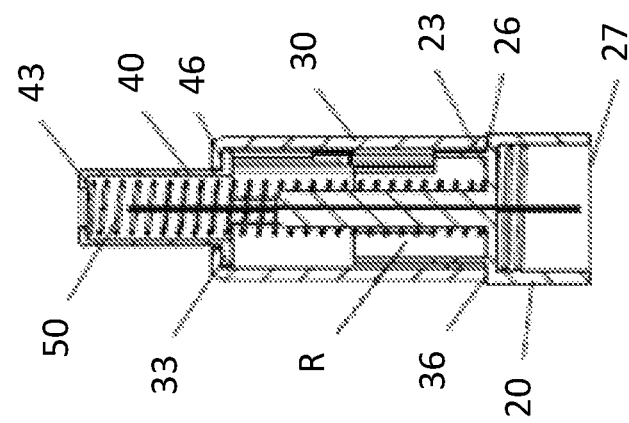
Figure 7A:
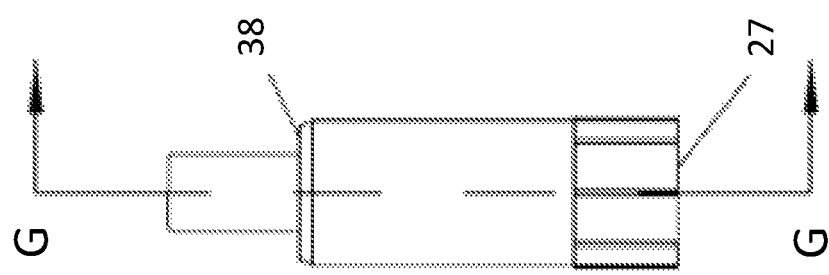
Figure 8:
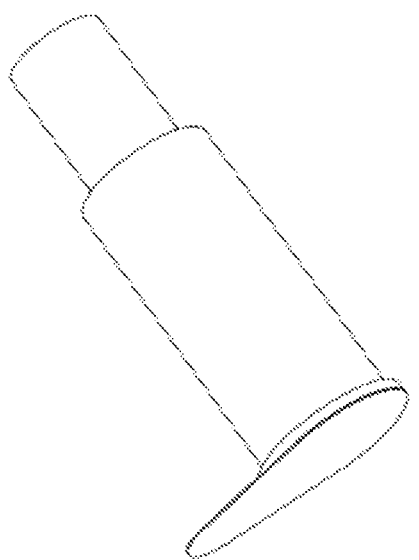
FIG. 8 is a stereoscopic view of the injection needle according to one exemplary embodiment of the present disclosure.

Referring to the above structure, the assembling process of the injection needle according to one aspect of the embodiments of the present disclosure, is described.

passing the tube needle 70 through the preset through-hole 21 inside the needle mount 20, and keeping it at a designated position, then fixing the tube needle 70 to the needle mount 20 by means of bonding, etc.;

sleeve-jointing the elastic element 50 to the elastic element limiting column 22 of the needle mount 20, with one end of the elastic element contacting with the elastic element limiting face 23 of the needle mount 20, and the internal diameter of the elastic element is slightly greater than the outer diameter of the elastic element limiting column to ensure that the elastic element may expand and contract freely;

causing the front end face 42 of the small sleeve (the second sleeve 40) to face the small sleeve limit face (the first blocking face) 33 of the auxiliary sleeve (the first sleeve 30), and ensuring that the sleeve limit arm 44 of the small sleeve is aligned with the limit arm guiding groove (corresponding to the first guiding groove 31, which is formed by both the guiding rib 35 and the guiding rib 39) of the small sleeve, wherein the small sleeve is placed into the auxiliary sleeve with the front end face 42 of the small sleeve passing through the through-hole of the auxiliary sleeve;

installing the component comprising the small sleeve and the auxiliary sleeve to the needle mount 20, and ensuring that the guiding rib 34 and the guiding rib 35 of the auxiliary sleeve are—placed in and along a notch 25 in an auxiliary sleeve engaging face 24 of the needle mount, until a bottom surface 36 of the auxiliary sleeve contacts with an auxiliary sleeve limit plane 26 of the needle mount 20, wherein since the outer diameter of the auxiliary sleeve engaging face 24 of the needle mount is slightly greater than the inner diameter of the needle mount engaging face 37 of the needle mount, the auxiliary sleeve can be steadily sleeve-jointed to the needle mount 20, and in the above case, referring to FIGS. 7a-7c, the other end of the elastic element prepositioned outside the elastic element limiting column 22 of the needle mount contacts with the elastic element limiting face (corresponding to the second spacing plane 43) of the small sleeve, while the limit face (corresponding to the step surface 46) of the small sleeve contacts with the small sleeve limit face of the auxiliary sleeve (the first blocking face 33), and as the free length of the elastic element is greater than the distance between the elastic element limiting face of the small sleeve and the elastic element limiting face of the needle mount, the position of the small sleeve is restricted by the support force of the elastic element and the auxiliary sleeve, the small sleeve will not move axially unless there is an external force is applied to the front end face 42 of the small sleeve;

sleeve-jointing the cavity opening 11 of the big sleeve to the needle outlet 41 of the small sleeve of the aforementioned component, the space between the needle mount end face 27 and the auxiliary sleeve front end face 38 is slightly smaller than that between the opening end face 13 of the big sleeve and the big sleeve shoulder 14, which allows a complete accommodation of the aforementioned component into the big sleeve, without affecting the engagement of the thread 28 inside the needle mount cavity with the insulin injection pen, in addition, the engaging bar 29 of the big sleeve on the needle mount surface is symmetrical distributed along the central axis, and the maximum spacing is slightly greater than the inner diameter of the cavity of the big sleeve, so that the big sleeve after being assembled is not prone to fall off from the needle mount while it can be easily picked off;

finally, fixing dialyzing paper to the end face of the outer sleeve opening by means of adhesion, etc., as shown in FIG. 8.

As shown in the figures, in an alternative embodiment of the present disclosure, the second sleeve 40 is provided with two guiding portions 42 and two limit arms 46, wherein the two limit arms 46 are arranged to be opposite to each other in the radial direction, and the two guiding portions 42 are arranged to be opposite to each other in the radial direction. As known to those of ordinary skill in the art, the fitting configuration on the first sleeve and the needle mount may be accordingly provided.

Referring to the above structure, the operating process of the injection needle, according to one aspect of the exemplary embodiment of the present disclosure, is described next.

Firstly, after removing the dialyzing paper 60, connecting the injection needle to the injection pen (not shown) by rotation, wherein an anti-rotating rib 12 is provided inside the big sleeve to prevent relative sliding between the big sleeve and the needle mount 20 and the resulted unstable connection, the anti-rotating rib 12 interferes with a big sleeve engagement rib 29 on the needle mount, so as to prevent relative sliding between the big sleeve and the needle mount.

Secondly, removing the big sleeve, and aligning the front end face 42 of the small sleeve with the injection site of the patient, wherein the small sleeve retracts toward inside the auxiliary sleeve at the time of being pressed, thus, the tube needle passes through the needle outlet 41 of the small sleeve, and after the guiding slope (corresponding to the sleeve guiding portion 48) of the small sleeve guiding arm 45 contacts with the small sleeve guiding face (corresponding to the guiding engagement portion 210) of the needle mount, referring to FIG. 9a-9d, the fastener 47 of the limit arm moves longitudinally in the guiding groove of the limit arm guiding groove (corresponding to the first guiding groove 31).

Then, causing the small sleeve to rotate during its axial retraction by a certain angle in the circumferential direction with respect to the needle mount (the angle is equal to the central angle between the guiding rib 34 and the guiding rib 35), and referring to FIGS. 10a-10d, the fastener 47 of the limit arm is rotated to move longitudinally inside the limit guiding slot 32 for the limit arm. Specifically, when the limit arm 44 of the small sleeve moves axially in the limit arm guiding groove (corresponding to the first guiding groove 31) of the auxiliary sleeve toward inside the auxiliary sleeve, the fastener 47 of the limit arm on the small sleeve gets close to the second guiding rib 39 (the second guiding rib 39 is divided axially into two portions, one of which close to the front end face has a rectangle section and the other of which has a trapezoidal section, the inclined face 310 faces the first guiding rib 35) and tends to move across the second guiding rib with the driving of the guiding arm (corresponding to the sleeve guiding arm 45), the contact face between the fastener 47 of the limit arm and the guiding rib 39 is the fastener slope 49, and when the contact portion between the fastener 47 of the limit arm and the second guiding rib 39 transits from a right angle face to the inclined face 310, the fastener 47 can easily move across the second guiding rib 39, and then stops inside the limit guiding slot 32 (formed by the second guiding rib 39 and the third guiding rib 34) for the limit arm of the auxiliary sleeve, as the fastener 47 continues to move axially until a stopping face (corresponding to the engagement blocking face 412) of the small sleeve contacts with an engaging stopping face (corresponding to the pressing blocking face 211) of the needle mount, and in this case, the elastic element is compressed, referring to FIGS. 11a-11b.

Figure 13:
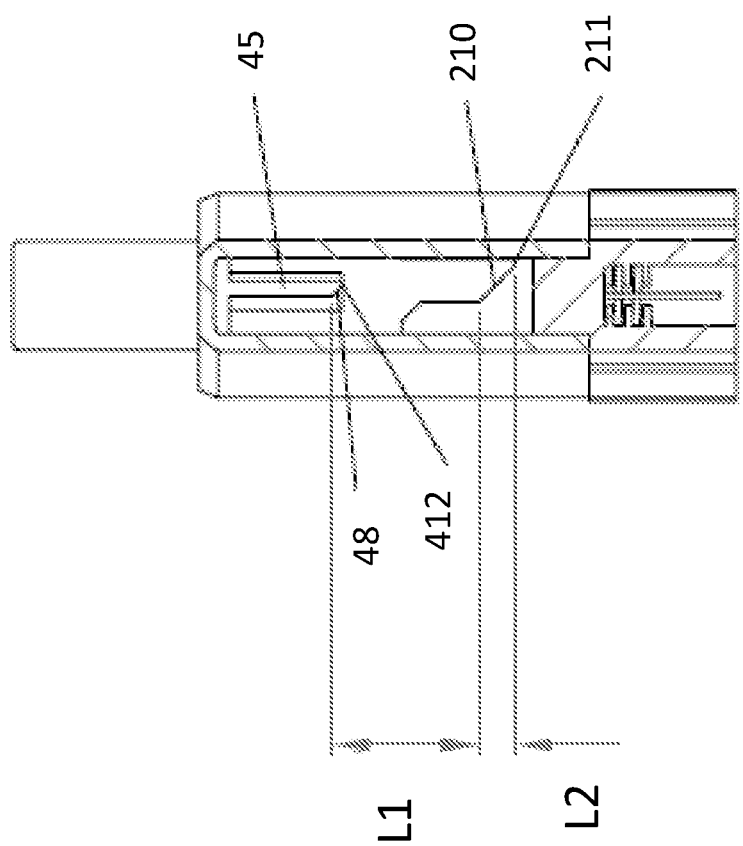
FIG. 13 schematically shows the displacement of the small sleeve from the beginning of retract to a rotating stop location of rotation.

FIG. 13 schematically shows the displacement of the small sleeve from the starting of retracting to the stop of rotating, illustratively, the small sleeve retracts for L1 in the first step (for example, 7.8 mm), and L2 (for example, 1.4 mm) during the rotation, with a total displacement of L1+L2 (for example, 9.2 mm).

Then, after the injection, once the tip of the tube needle is pulled out, the elastic element provides a reset force for the small sleeve, the fastener 47 of the limit arm on the small sleeve moves along the limit guiding slot 32 for the limit arm, at the middle of the limit guiding slot for the limit arm of the auxiliary sleeve (where the small sleeve can be supported to prevent the tube needle from exposing and the fastener is close to one end of the second guiding rib with the rectangular section) is a limit boss (corresponding to the blocking member 311) provided, the limit boss is compliant with respect to the first contact face (corresponding to the compliant face 312) of the fastener 47 of the limit arm, while is uncompliant with respect to the second contact surface (corresponding to blocking face 313) of the fastener, and the first contact surface (corresponding to the compliant face 410) of the fastener 47 of the limit arm on the small sleeve is also compliant, so that the limit arm 44 may move across the limit boss of the auxiliary sleeve upon a tiny elastic deformation during its restoration; in addition, the second contact face (corresponding to the blocking face 411) of the fastener 47 of the limit arm is uncompliant with respect to a second contact face of the limit boss and has the same angle as that of the second contact face of the limit boss of the auxiliary sleeve, thus, if a secondary use of the injection needle is intended and force is applied to the front end face 42 of the small sleeve, the fastener 47 of the limit arm on the small sleeve abuts against the limit boss of the auxiliary sleeve, leading to a failure of the injection needle, referring to FIGS. 12a-12c.

The disposable injection needle of the present disclosure can be used for cooperating with an insulin injection pen for the subcutaneous injection of insulin for the diabetics. As known to those of ordinary skill in the art, the disposable injection needle of the present disclosure can also be used cooperating with other injection pens or medical instrument.

Though the embodiments of the present disclosure have been shown and described, for those of ordinary skill in the art, it is appreciated that these embodiments can be changed without departing from the principles and spirit of the present disclosure, and the scope of the present disclosure is defined by the appended claims and any and all equivalents thereof.

The invention claimed is:

1. A disposable injection needle, including:
   a needle mount provided with a tube needle that extends axially therethrough;
   a first sleeve, one end of which is suitable for connecting to one end of the needle mount to form receiving space between the first sleeve and the needle mount, and the other end of which is provided with a first opening;
   a second sleeve, one end of which is located inside the receiving space, and the other end of which having a second opening extends out from the first opening, wherein part of the second sleeve is provided, in an axially slideable manner, inside the receiving space, and the tube needle is adapted to protrude through the second opening; and
   an elastic element adapted to provide elastic force for the second sleeve to move axially toward outside the receiving space, wherein the second sleeve is adapted to retract inward the receiving space based on an external force overcoming the elastic force, so as to expose the tube needle,
   wherein:
   the second sleeve is provided with a sleeve guiding portion, the needle mount or first sleeve is provided with a guiding engagement portion, the sleeve guiding portion engages with the guiding engagement portion to guide circumferential rotation of the second sleeve based on axial movement of the second sleeve toward inside the receiving space;
   the first sleeve is provided with a blocking member and the second sleeve is provided with a fastener, wherein the blocking member and the fastener are arranged to allow the fastener to pass through the blocking member in the axial direction toward the second opening, and to prevent the fastener from passing through the blocking member in the axial direction away from the second opening to prevent the tube needle from being exposed via the second opening;
   the needle mount is provided with the guiding engagement portion;
   the needle mount is provided with a needle mount guiding portion the end of which is provided with a needle mount guiding slope which constitutes the guiding engagement portion;
   the second sleeve includes a sleeve guiding arm which is adapted to move axially and circumferentially inside the needle mount guiding portion, and the end of the sleeve guiding arm is provided with an engaging slope which engages with the needle mount guiding slope and which constitutes the sleeve guiding portion; and
   the distance or the width of the needle mount guiding portion is greater than that of the sleeve guiding arm in the circumferential direction, so as to allow the second sleeve to complete the circumferential rotation.

2. The disposable injection needle according to claim 1, wherein:
   the inner wall of the first sleeve is provided with a limit guiding slot in which the blocking member is provided; and
   the fastener is adapted to enter the limit guiding slot due to the rotation of the second sleeve in circumferential direction.

3. The disposable injection needle according to claim 2, wherein: the inner wall of the first sleeve is provided with a first guiding rib, a second guiding rib and a third guiding rib which extend in the axial direction and are spaced apart from one another and parallel to one another, wherein a first guiding groove is formed between the first guiding rib and the second one, and a second guiding groove, constituting the limit guiding slot, is formed between the second guiding rib and the third guiding rib; due to the circumferential rotation, the fastener is adapted to move circumferentially from the first guiding grove to the second guiding grove.

4. The disposable injection needle according to claim 2, wherein:
   the second sleeve is provided with a sleeve limit arm, whose end is provided with the fastener.

5. The disposable injection needle according to the claim 3, wherein:
corresponding to the circumferential movement, one side of the second guiding rib facing the first guiding groove is provided with a face that facilitates moving of the fastener across the second guiding rib; and/or
one side of the fastener facing the second guiding rib is provided with a face that facilitates moving of the fastener across the second guiding rib.

6. The disposable injection needle according to claim 5, wherein:
the cross section of the portion of the second guiding rib, from the blocking member to the first opening, is a rectangle, and the cross section of the portion of the second guiding rib, from the blocking member to the end of the first sleeve, is a right trapezoid, with the hypotenuse of the right trapezoid facing the first guiding groove, optionally, the side of the fastener facing the second guiding rib when the fastener is in the first guiding groove is provided with a fastener slope.

7. The disposable injection needle according to claim 1, wherein:
the end of the needle mount guiding portion is additionally provided with a pressing blocking face connected to the needle mount guiding slope;
the end of the sleeve guiding arm is provided with an engagement blocking face which is connected to the engaging slope, and which abuts against the pressing blocking face to prevent the second sleeve from moving axially further after the second sleeve completes its circumferential rotation.

8. The disposable injection needle according to claim 1, wherein:
the first sleeve is provided with a guiding groove and a limit guiding slot;
the first sleeve is provided with the guiding engagement portion, which is an inclined guiding slot or a cambered guiding slot connecting the end of the guiding groove and that of the limit guiding slot;
the second sleeve includes a sleeve guiding arm, wherein the fastener is provided at the end of the sleeve guiding arm, and the blocking member is provided inside the limit guiding slot; and
the fastener is adapted to enter the limit guiding slot via the inclined guiding slot or the cambered guiding slot due to the circumferential rotation.

9. The disposable injection needle according to claim 1, wherein:
the first end of the needle mount is provided with an elastic element limiting column, which extends axially from the first end of the needle mount, and through which the tube needle extends axially;
the other end of the second sleeve has a second blocking face which is perpendicular to the axis and defines the second opening;
the elastic element includes a spring one end of which is provided to the elastic element limiting column and the other end of which presses against the second blocking face.

10. The disposable injection needle according to claim 1, wherein:
one end of the second sleeve is located inside the receiving space and the other end of the second sleeve is provided with the second opening and extends out from the first opening, and one part of the second sleeve is provided in an axially slideable manner inside the receiving space.

11. The disposable injection needle according to claim 10, wherein:
the second sleeve has a small-diameter section and a large-diameter section connected to each other axially, a step surface is formed at the junction therebetween, wherein, the small-diameter section is suitable for axially extending out of the first sleeve from the first opening, and the distal end of the small-diameter section has the second opening and a second blocking face which is perpendicular to the axis and defines the second opening, the step surface is adapted to abut against a first blocking face, and the large-diameter section is provided in an axially slideable manner inside the receiving space.

12. The disposable injection needle according to claim 1, wherein:
the first end of the needle mount is additionally provided with an engaging circumferential surface;
one end of the first sleeve is suitable for being sleeve-jointed to the engaging circumferential surface.

13. The disposable injection needle according to claim 1, further including:
a third sleeve, which sleeve-joints the needle mount, the first sleeve and the second sleeve from outside.

14. The disposable injection needle according to claim 1, wherein:
the other end of the needle mount is provided with a connecting device suitable to connect with the injection pen.

15. The disposable injection needle according to claim 1, wherein:
the second sleeve is provided with two guiding portions and two limit arms, wherein the two limit arms are arranged to be opposite to each other in the radial direction, and the two guiding portions are arranged to be opposite to each other in the radial direction.

16. A disposable injection needle comprising:
a needle mount provided with a tube needle that extends axially therethrough;
a first sleeve, one end of which is suitable for connecting to one end of the needle mount to form receiving space between the first sleeve and the needle mount, and the other end of which is provided with a first opening;
a second sleeve, one end of which is located inside the receiving space, and the other end of which having a second opening extends out from the first opening, wherein part of the second sleeve is provided, in an axially slideable manner, inside the receiving space, and the tube needle is adapted to protrude through the second opening; and
an elastic element adapted to provide elastic force for the second sleeve to move axially toward outside the receiving space, wherein the second sleeve is adapted to retract inward the receiving space based on an external force overcoming the elastic force, so as to expose the tube needle,
wherein:
the second sleeve is provided with a sleeve guiding portion, the needle mount or first sleeve is provided with a guiding engagement portion, the sleeve guiding portion engages with the guiding engagement portion to guide circumferential rotation of the second sleeve based on axial movement of the second sleeve toward inside the receiving space;
the first sleeve is provided with a blocking member and the second sleeve is provided with a fastener, wherein the blocking member and the fastener are arranged to allow the fastener to pass through the blocking member in the axial direction toward the second opening, and to prevent the fastener from passing through the blocking member in the axial direction away from the second opening to prevent the tube needle from being exposed via the second opening;

the inner wall of the first sleeve is provided with a limit guiding slot in which the blocking member is provided;

the fastener is adapted to enter the limit guiding slot due to the rotation of the second sleeve in circumferential direction; the second sleeve is provided with a sleeve limit arm, whose end is provided with the fastener;

the second sleeve is provided with a sleeve limit arm, whose end is provided with the fastener;

the side of the fastener facing the second opening is set as a compliant face, and the other side of the fastener facing the compliant face in the axial direction is set as a blocking face; and the side of the blocking member facing the first opening is set as a blocking face engaging with the blocking face of fastener; or, the side of the blocking member facing the first opening is set as a blocking face engaging with the blocking face of fastener, and the other side of the blocking member opposite to its blocking face in the axial direction is provided with a compliant face cooperating with the compliant face of the fastener.

17. A disposable injection needle comprising:

a needle mount provided with a tube needle that extends axially therethrough;

a first sleeve, one end of which is suitable for connecting to one end of the needle mount to form receiving space between the first sleeve and the needle mount, and the other end of which is provided with a first opening;

a second sleeve, one end of which is located inside the receiving space, and the other end of which having a second opening extends out from the first opening, wherein part of the second sleeve is provided, in an axially slideable manner, inside the receiving space, and the tube needle is adapted to protrude through the second opening;

an elastic element adapted to provide elastic force for the second sleeve to move axially toward outside the receiving space, wherein the second sleeve is adapted to retract inward the receiving space based on an external force overcoming the elastic force, so as to expose the tube needle, and a third sleeve, which sleeve-joints the needle mount, the first sleeve and the second sleeve from outside, wherein:

the second sleeve is provided with a sleeve guiding portion, the needle mount or first sleeve is provided with a guiding engagement portion, the sleeve guiding portion engages with the guiding engagement portion to guide circumferential rotation of the second sleeve based on axial movement of the second sleeve toward inside the receiving space;

the first sleeve is provided with a blocking member and the second sleeve is provided with a fastener, wherein the blocking member and the fastener are arranged to allow the fastener to pass through the blocking member in the axial direction toward the second opening, and to prevent the fastener from passing through the blocking member in the axial direction away from the second opening to prevent the tube needle from being exposed via the second opening; and a first anti-rotational mechanism is provided at the junction between the first sleeve and the needle mount, and a second anti-rotational mechanism is provided at the junction between the third sleeve and the needle mount.

* * * * *